(12) United States Patent
Eriksson

US008501419B2

(10) Patent No.: US 8,501,419 B2
(45) Date of Patent: Aug. 6, 2013

(54) EXPOSED PROLIFERATION-RELATED PEPTIDES, LIGANDS AND METHODS EMPLOYING THE SAME

(75) Inventor: Staffan Eriksson, Stockholm (SE)

(73) Assignee: Arocell AB, Uppsala (SE)

( * ) Notice: Subject to any disclaimer, the term of this patent is extended or adjusted under 35 U.S.C. 154(b) by 206 days.

(21) Appl. No.: 12/601,326

(22) PCT Filed: May 23, 2008

(86) PCT No.: PCT/IB2008/052051
§ 371 (c)(1),
(2), (4) Date: Nov. 23, 2009

(87) PCT Pub. No.: WO2008/142664
PCT Pub. Date: Nov. 27, 2008

(65) Prior Publication Data
US 2010/0173329 A1    Jul. 8, 2010

Related U.S. Application Data

(60) Provisional application No. 60/931,443, filed on May 23, 2007.

(51) Int. Cl.
*G01N 33/53* (2006.01)
*G01N 33/567* (2006.01)
*G01N 33/574* (2006.01)

(52) U.S. Cl.
USPC .......................... 435/7.2; 435/7.21; 435/7.23

(58) Field of Classification Search
None
See application file for complete search history.

(56) References Cited

U.S. PATENT DOCUMENTS 6,083,707 A * 7/2000 Eriksson et al. ............... 435/7.4
7,442,513 B2 * 10/2008 Worley ........................... 435/7.1
2006/0035295 A1 2/2006 Oehrvik et al.
2007/0141650 A1 * 6/2007 Skog et al. .................... 435/7.23

FOREIGN PATENT DOCUMENTS
WO 95/29192 A1 11/1995

OTHER PUBLICATIONS

Zhang et al, Hybridoma, 20(1):25-34 (2001).
Welin et al, Proceedings of the National Academy of Sciences of the United States of America, 101(52):17970-17975 (2004).
Zhang et al, Oncology Reports, 15(2):455-461 (Feb. 2006).
Wu et al, Journal of Immunological Methods, Elsevier Science Publishers BV, Amsterdam, NL, 277(1-2):157-169 (2003).
Kuroiwa et al, Journal of Immunological Methods, Elsevier Science Publishers BV, Amsterdam, NL, 253(1-2):1-11 (2001).
He et al, European Journal of Cell Biology, Wissenschafliche Verlagsgesellschaft, Stuttgart, DE, 70:117-124 (1996).
Gronowitz et al, "The Use of Serum Desoxythymidine Kinase as a Prognostic Marker, and in the Monitoring of Patients with Non-Hodgkin's Lymphoma," British Journal of Cancer, vol. 47, pp. 487-495, 1983.
Flemington et al, "Sequence, Structure and Promoter Characterization of the Human Thymidine Kinase Gene," Gene, vol. 52, pp. 267-277, 1987.
Karlström, et al, "Molecular Forms in Human Serum of Enzymes Synthesizing DNA Precursors and DNA," Molecular and Cellular Biochemistry, vol. 92, pp. 23-35, 1990.
Hallek, et al, "Thymidine Kinase: A Tumor Marker with Prognostic Value for Non-Hodgkin's Lymphoma and a Broad Range of Potential Clinical Applications," Annals of Hematology, vol. 65, pp. 1-5, 1992.
Törnevik, et al, Cytotoxicity of 3'-Azido-3'-Deoxythymidine Correlates with 3'-Azidothymidine-5'-Monophosphate (AZTMP) Levels, Whereas Anti-Human Immunodeficiency Virus (HIV) Activity Correlates with 3'-Azidothymidine-5'-Triphosphate (AZTTP) Levels in Cultured CEM T-Lymphoblastoid Cells, Biochemical Pharmacology, vol. 49, No. 6, pp. 829-837, 1995.
Hallek, et al, Elevated Serum Thymidine Kinase Levels Identify a Subgroup at High Risk of Disease Progression in Early, Nonsmoldering Chronic Lymphodytic Leukemia, Blood, vol. 93, No. 5, pp. 1732-1737, Mar. 1, 1999.
He, et al, "The Clinical Significance of Thymidine Kinase 1 Measurement in Serum of Breast Cancer Patients Using Anti-TK1 Antibody," The International Journal of Biological Markers, vol. 15, No. 2, pp. 139-146, 2000.
Wu, et al, "A New Cell Proliferating Marker: Cytosolic Thymidine Kinase as Compared to Proliferating Cell Nuclear Antigen in Patients with Colorectal Carcinoma," AntiCancer Research, vol. 20, pp. 4815-4820, 2000.
Wang, et al, "Investigation on Cell Proliferation with a New Antibody Against Thymidine Kinase 1," Analytical Cellular Pathology, vol. 23, pp. 11-19, 2001.
Foekens, et al, "Thymidine Kinase and Thymidylate Synthase in Advanced Breast Cancer: Response to Tamoxifen and Chemotherapy," Cancer Research, vol. 61, pp. 1421-1425, Feb. 15, 2001.
Broët, et al, "Thymidine Kinase as a Proliferative Marker: Clinical Relevance in 1,692 Primary Breast Cancer Patients," Journal of Clinical Oncology, vol. 19, No. 11, pp. 2778-2787, Jun. 1, 2001.

(Continued)

*Primary Examiner* — Mark Navaro
*Assistant Examiner* — Khatol Shahnan-Shah
(74) *Attorney, Agent, or Firm* — Porter Wright Morris & Arthur LLP (57) ABSTRACT

Novel thymidine kinase (TK1) derived peptide consisting of the amino acid sequence of SEQ ID NO:1 or SEQ ID NO:2 is employed to obtain ligands having specificity to the peptide. The ligand may be an antibody or fragment thereof and may be used in various methods and kits for health screening and the like.

29 Claims, 6 Drawing Sheets

OTHER PUBLICATIONS

Zou, et al, "The Half-Life of Thymidine Kinase 1 in Serum Measured by ECL Dot Blot: A Potential Marker for Monitoring the Response to Surgery of Patients with Gastric Cancer," The International Journal of Biological Markers, vol. 17, No. 2, pp. 135-140, 2002.

Eriksson, et al, "Structure and Function of Cellular Deoxyribonucleoside Kinases," Cellular and Molecular Life Sciences, vol. 59, pp. 1327-1346, 2002.

Mao, et al, "A Comparative Study: Immunohistochemical Detection of Cytosolic Thymidine Kinase and Proliferating Cell Nuclear Antigen in Breast Cancer," Cancer Investigation, vol. 20, Nos. 7 & 8, pp. 922-931, 2002.

Öhrvik, et al, "Sensitive Nonradiometric Method for Determining Thymidine Kinase I Activity," Clinical Chemistry, vol. 50, No. 9, pp. 1597-1606, 2004.

Ke, et al, "Mitotic Degradation of Human Thymidine Kinase 1 is Dependent on the Anaphase-Promoting Complex/Cyclosome-Cdh1-Mediated Pathway," Molecular and Cellular Biology, vol. 24, No. 2, pp. 514-526, Jan. 2004.

He, et al, "Thymidine Kinase 1 in Serum Predicts Increased Risk of Distant of Loco-Regional Recurrence Following Surgery in Patients with Early Breast Cancer," AntiCancer Research, vol. 26, pp. 4753-4760, 2006.

\* cited by examiner

Immunocytochemistry (Formalin-fixed Hela cells)

XPA 210 antiTK1 antibody    XPA 161 antiTK1 antibody

SEQUENCE LISTING

```
<160> NUMBER OF SEQ ID NOS: 3

<210> SEQ ID NO 1
<211> LENGTH: 23
<212> TYPE: PRT
<213> ORGANISM: Homo sapiens
<220> FEATURE:
<221> NAME/KEY: MISC_FEATURE
<222> LOCATION: (23)..(23)
<223> OTHER INFORMATION: Xaa is Ser-NH2
```

-continued

```
<400> SEQUENCE: 1

Ala Tyr Thr Lys Arg Leu Gly Thr Glu Lys Glu Val Glu Val Ile Gly
1               5                   10                  15

Gly Ala Asp Lys Tyr His Xaa
            20

<210> SEQ ID NO 2
<211> LENGTH: 23
<212> TYPE: PRT
<213> ORGANISM: Homo sapiens

<400> SEQUENCE: 2

Ala Tyr Thr Lys Arg Leu Gly Thr Glu Lys Glu Val Glu Val Ile Gly
1               5                   10                  15

Gly Ala Asp Lys Tyr His Ser
            20

<210> SEQ ID NO 3
<211> LENGTH: 31
<212> TYPE: PRT
<213> ORGANISM: Homo sapiens
<220> FEATURE:
<221> NAME/KEY: MISC_FEATURE
<222> LOCATION: (31)..(31)
<223> OTHER INFORMATION: Xaa is Gln-OH

<400> SEQUENCE: 3

Gly Gln Pro Ala Gly Pro Asp Asn Lys Glu Asn Cys Pro Val Pro Gly
1               5                   10                  15

Lys Pro Gly Glu Ala Val Ala Ala Arg Lys Leu Phe Ala Pro Xaa
            20                  25                  30
```

EXPOSED PROLIFERATION-RELATED PEPTIDES, LIGANDS AND METHODS EMPLOYING THE SAME

RELATED APPLICATIONS

The present application is a 371 of PCT/IB2008/052051 filed May 23, 2008 and claims priority under 35 U.S.C. §119 of U.S. Application No. 60/931,443 filed May 23, 2007.

FIELD OF THE INVENTION

The present invention is directed to a novel thymidine kinase 1 (TK1) derived peptides, ligands, including antibodies thereof, and methods of employing the same.

BACKGROUND OF THE INVENTION

Cancer is a leading cause of death in humans and a major medical need is to be able to detect early signs of the disease and monitor the success of treatments. Serum tumor markers have been used for these purposes for more than 30 years. Thymidine kinase 1 protein (TK1) is a cytosolic enzyme involved in the synthesis of DNA precursors and it is only expressed in proliferating cells, i.e., in cells in the S phase of the cell cycle. This enzyme is a classic marker for cell proliferation and its regulation and properties have been studied extensively during the last 40 years (1). It was discovered that a form of TK1 was found in the serum of animals and humans with a high proportion of proliferating cells, e.g., in patients with some type of infection or tumor disease. Sensitive radioisotope methods were developed and used to determine the level of active TK1 in serum from patients with different types of diseases (2-4). The clinical value of determination of serum TK1 as a tumor marker in monitoring hematologic cancers has been well established and a commercial cancer marker kit has been available (Prolifigen® TK-REA from DiaSorin) with applications in non-Hodgkin's lymphoma, Hodgkin's disease, chronic lymphocytic leukemia, acute lymphocytic leukemia, acute myeloic leukemia and multiple myeloma (2-4). Furthermore, measuring TK activity in cytosolic breast tumor extracts has given relatively good prognostic information as a tumor marker (5, 6). However, drawbacks of the Prolifigen® assay are that it is relatively complex and dependent on radio-isotopes and as a serum marker it is limited in use as only hematologic malignancies can be monitored.

More recently, an alternative non-radioactive TK activity assay was developed based on the high capacity of TK1 to phosphorylate the stable substrate analog 3'-azido-thymidine. The product of this reaction, AZTMP, was determined using polyclonal antibodies directed against AZTMP (7). A fully automated competitive chemiluminescence assay has been developed (Liason thymidine kinase) and is commercially available from DiaSorin AB for the same applications as those described above (8). A complex but sensitive non radioactive immunoassay (DiviTum®), based on the phosphorylation and incorporation of 5-bromo-deoxyuridine into an oligonucleotide, has recently been placed on the market for the follow up of lymphomas and leukemia by Biovica AB (9). The main drawbacks of these methods are the limitation of their application to hematologic malignancies and their dependence on time-consuming enzyme reaction measurements. Further, the Liason thymidine kinase assay requires the use of special instrumentation and the DiviTum® assay requires a long process time.

In recent years, several different monoclonal and polyclonal antibodies directed against TK1 have been described (10-16). The most specific and sensitive TK1 antibodies which have been produced for use in serum TK determinations rely on TK1-peptides representing 15 or 31-amino acids fragments of a certain amino acid sequence in the C-terminal part of TK1 (10, 13). This epitope domain has been named exposed proliferation antigen 210 (XPA210) based on the numbering of the central amino acid in the TK1 peptide sequence. Recently, several studies were published where the level of TK1 in cells and serum were determined by immunological methods using these antibodies and it became clear that the activity and the immunological assays did not correlate but appeared to provide complementing information regarding cell proliferation (15,16 and unpublished results). It was also clear that intact TK1 is poorly immunogenic and the quality of several earlier described antibodies are questionable. The method to produce the TK1 specific antibodies is disclosed in U.S. Pat. No. 6,083,707. The same procedure but using a longer peptide (31 instead of 15 amino acid fragments) has also been disclosed (12). The introduction of methods using XPA210 have led to production of clearly defined immunological reagents that have served as the basis for studies demonstrating that TK1 immunoreactive material can be used to monitor a large number (at least 10 different types) of tumor diseases including breast, lung, bladder, etc. (10-16). Furthermore, based on XPA210 measurements, the recurrence of certain solid tumors (e.g. breast carcinomas) could be predicted several years before other signs of disease could be detected (17). A dot blot immunoassay as well as a histochemistry kit based on this type of purified polyclonal antibodies are available from ssTK Inc (18).

A major problem encountered in many immunological assays is that they may lack sensitivity by masking of epitopes on the antigen in certain situations and/or cross-reactivity of antigen to other proteins occurs.

SUMMARY OF THE INVENTION

Accordingly, it is an object of the invention to provide further developments with respect to TK1 determination.

In one embodiment, the present invention is directed to a peptide having an amino acid sequence according to SEQ ID NO:1, set forth as Ala-Tyr-Thr-Lys-Arg-Leu-Gly-Thr-Glu-Lys-Glu-Val-Glu-Val-Ile-Gly-Gly-Ala-Asp-Lys-Tyr-His-Ser-NH2. This peptide is referred to herein as XPA161. In another embodiment, the invention is directed to a peptide having an amino acid sequence according to SEQ ID NO. 2, set forth as Ala-Tyr-Thr-Lys-Arg-Leu-Gly-Thr-Glu-Lys-Glu-Val-Glu-Val-Ile-Gly-Gly-Ala-Asp-Lys-Tyr-His-Ser.

In other embodiments, the invention is directed to a ligand, for example, an antibody, having specificity for such a peptide, including fragments of such an antibody which bind to the peptide.

In yet additional embodiments, the invention is directed to methods employing such ligands, for example, antibodies and/or fragments thereof. One such method is for determining a level of immunoreactive material in a sample and comprises contacting the sample with the ligand, which in a specific embodiment is an antibody or a fragment thereof, and detecting the amount of bound ligand. Another such method is for estimating the likelihood of recurrence of a tumor in an individual and comprises determining a level of immunoreactive material in a sample from the individual by contacting the sample with the ligand, which in a specific embodiment is an antibody or a fragment thereof, and detecting the amount of bound ligand, and comparing the determined level with a level of immunoreactive material representative of a population of healthy persons or with a level of immunoreactive material previously determined in the same individual.

In an additional embodiment, the invention is directed to methods for determining cell proliferation in a sample, which methods comprise contacting the sample with the ligand, and detecting the amount of bound ligand. In a further embodiment, the invention is directed to methods of determining a level of inflammation, infection, or tumor cell proliferation in an individual, which methods comprise contacting a sample from the individual with the ligand, and detecting the amount of bound ligand.

In another embodiment, the present invention is directed to methods of performing a health screening test for an individual to detect accelerated cell proliferation. These methods comprise determining a level of immunoreactive material in a sample from the individual by contacting the sample with the ligand and detecting the amount of bound ligand, and comparing the determined level with a level of immunoreactive material representative of a population of healthy persons or with a level of immunoreactive material previously determined in the same individual. In specific embodiments of these methods, the ligand is an antibody having specificity to the peptide of SEQ ID NO: 1 or SEQ ID NO: 2, or is a fragment of such an antibody, which fragment binds to the peptide of SEQ ID NO: 1 or SEQ ID NO: 2.

The invention is also directed to kits comprising the ligand to determine a level of normal or tumor cell proliferation in an individual using the ligand. The kit may optionally contain at least one additional TK or ligand having different specificity.

Additional embodiments of the invention, and various advantages thereof, will be more apparent in view of the following Detailed Description.

BRIEF DESCRIPTION OF THE DRAWINGS

The invention and the Detailed Description will be more fully understood in view of the drawings, in which:

FIGS. 1A-1D show the sequence, structure and antigen design of human TK1. Specifically.

FIG. 2 shows immunoprecipitation of TK1 with XPA161 and XPA210 IgY. TK1 activity was determined as described in Example 1 and cell extracts from human T-lymphoblastoid CEM cells negative and positive (wild type) with respect to TK1, as well as supernatants (s) and the pelleted (p) HighTrap IgY binding beads were tested.

FIGS. 3A and 3B show analysis using XPA161 IgY and XPA210 IgY. Specifically, FIG. 3A shows western blot analysis of CEM cell extracts using XPA161 IgY and XPA210 IgY. Native PAGE analysis and blotting of proteins from human T-lymphoblastoid CEM cells, negative (C−) and positive (C+) for TK1 were performed as described in Example 1. The blotted filter strips were incubated without primary antibody (1), with XPA161 IgY (2), with XPA210 IgY, immunized with peptide alone (3), and with XPA210 IgY, immunized with peptide coupled to KLH (4), respectively. The arrow indicates the position of the TK1 tetramer (see reference 12). FIG. 3B shows SDS-PAGE analysis. Wells 1-3 contained 2, 1 and 0.5 ng pure recombinant human TK1, well 4 contained 40 µg proteins from CEM positive cells, and well 5 contained 40 µg proteins from CEM negative cells. Standard molecular weight markers for SDS-PAGE were run in the same gel and the positions corresponding to 25, 50 and 75 kDa are indicated. Blotted filers were incubated with XPA 161 mouse hybridoma supernatant IgG (2 µg/ml) and processed for enhanced chemoluminescence (ECL) detection.

DETAILED DESCRIPTION

Figure 1A:
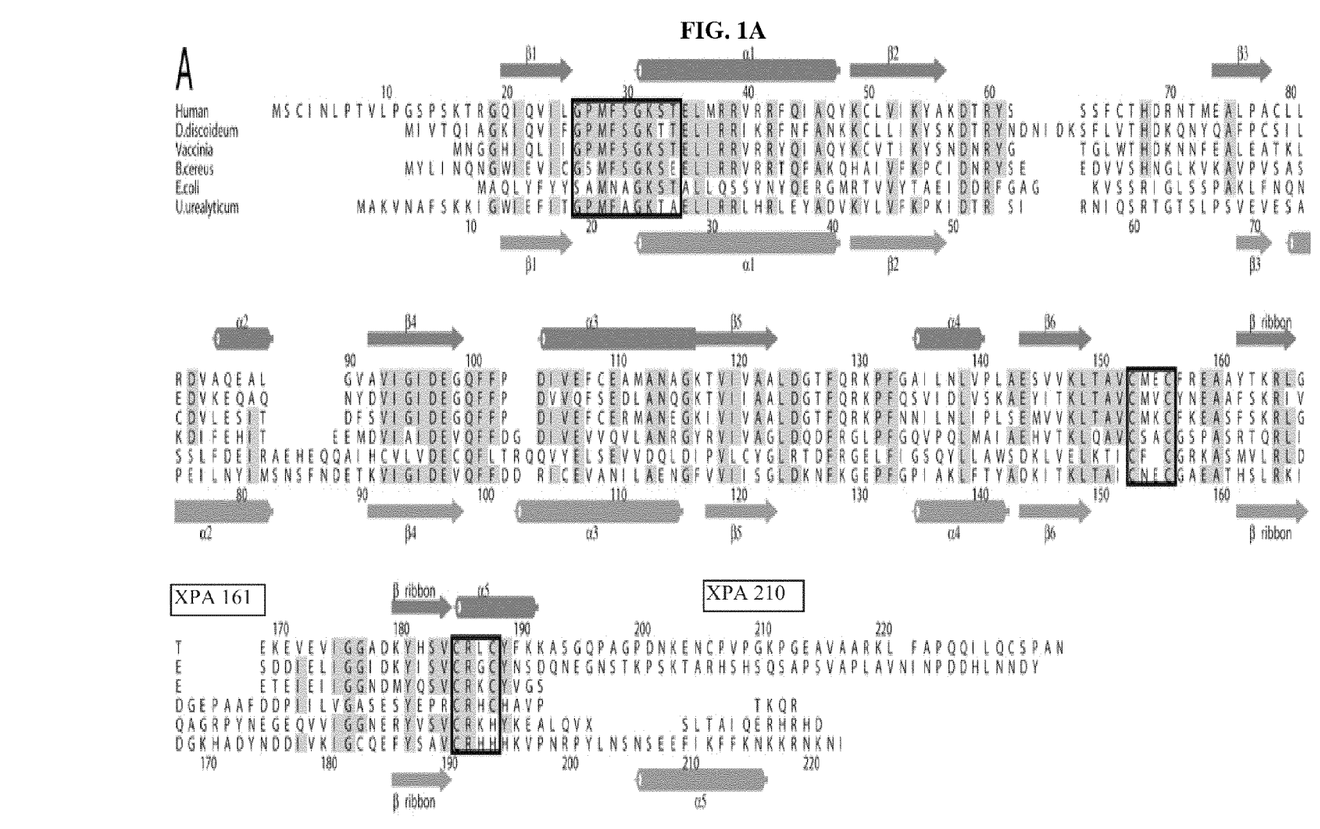
FIG. 1A shows the structural alignment of the sequences of TKs from human (P04183), *Dictyostelium discoideum* (AAB03673.1), Vaccinia virus (AAB96503.1), *B. cereus* (ZP_00241105.1), *E. coli* (NP_287483.1), and *U. urealyticum* (*U. parvum*) (NP_078433). Secondary structure elements for hTK1 are shown above the alignment and those for Uu-TK are shown below the alignment. The P loop and the two zinc co-ordinating sequences are boxed. The original figure is from reference 19. The sequences corresponding to XPA161 and XPA210 are shown with text boxes.
Figure 1B:
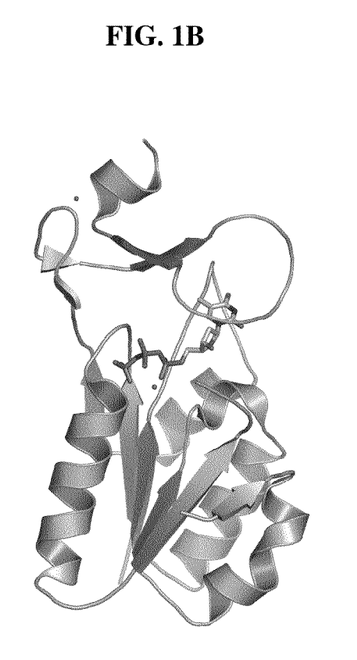
FIG. 1B shows the monomer structure of human TK1 with dTTP bound in the active site; the loop segment covering the active site corresponds to the XPA161 peptide as indicated by the box.
Figure 1C:
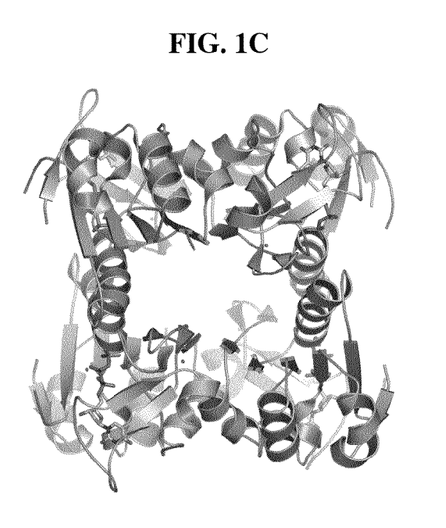
FIG. 1C shows the structure of the TK1 tetramer.

The structures of human TK1 and a bacterial TK (from *Ureoplasma urealyticum*, Uu) have been previously published (19). Both TK structures are tetramers, and each subunit consists of two domains, one alfa/beta-domain and a small zinc-containing domain. The active site is situated between these domains (FIG. 1A). The alfa/beta-domain of TK1 is of the same type as ATP-binding domains in enzymes of the RecA-F1ATPase family and is present in several DNA metabolizing proteins. The active site consists of a small domain of 70-80 aa, contains a long, lasso-shaped structure (FIG. 1A, B). No similar structure has been found in other known proteins so far. The domain contains two beta-ribbons connected via a zinc ion and the lasso-shaped loop binds the base of the nucleoside substrate.

Figure 1D:
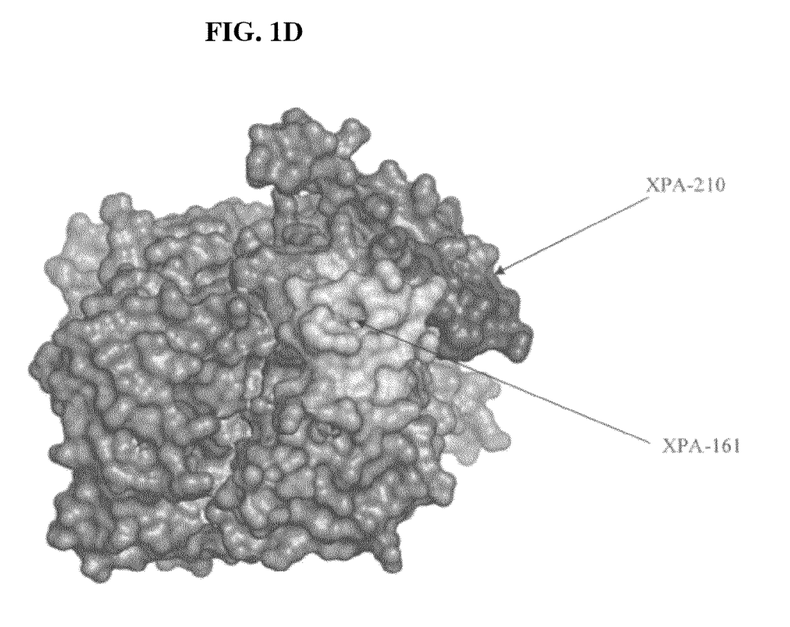
FIG. 1D shows the structural model of the TK1 holo-enzyme tetramer (Welin M and Eriksson S) with both the XPA161 segment and the XPA210 segment indicated.

Unfortunately, human TK1 used in the crystallization is a truncated enzyme lacking the 40 C-terminal amino acids and thus the XPA210 peptide. In the full-length Uu-TK enzyme, the C-terminal structure, with an extended arm-like loop and a terminal helix, can be seen and the C-terminal helix interacts with a helix on the adjacent monomer, probably helping to keep the tetramer together. Secondary sequence predictions strongly suggest that a similar extended arm and a C-terminal helix is found also in the human enzyme. A model of full length human TK1 is presented in FIG. 1D. The missing C terminus of human TK1 contains a sequence motif (KEN) that serves as an ubiquitination ligase signal involved in the cell cycle dependent degradation of TK1 (20). The capacity of XPA210 to serve as an exposed and highly effective TK1 epitope can thus be explained. It is also evident that only intact TK1 contains the XPA210 epitope.

Based on the structure of human TK1 (and Uu TK), a new peptide starting at Ala161 and ending at Ser183 (FIGS. 1A, 1B and 1D), a 23 amino acid peptide that corresponds to the lasso domain, was designed and synthesized. This peptide has been named XPA 161 (SEQ ID NO: 1). A similar peptide, without a terminal NH2, is also within the scope of the peptides of the present invention as disclosed herein. This active site domain is still in an exposed position but clearly distinct from that of XPA210 as shown in the model presented in FIG. 1D. A cysteine residue may be added to the N-terminal of this peptide to create a 24 mer peptide. The present invention is also directed to ligands having specificity to such peptides. In one embodiment, the ligands are antibodies or fragments thereof exhibiting specificity to the peptides. In other embodiments the ligands may comprise single domains, engineered scaffolds, nucleic acid aptamers or the like which exhibit specificity for the inventive peptides.

As described in examples herein, the XPA161 peptide may be cross-linked onto a carrier protein, for example, Keyhole Limpet Hemocyanin (KLH) or alternatively Bovine Serum Albumin (BSA). In examples described below, a complex of XPA161-KLH was mixed with adjuvants and used for immunization of chickens. Crude IgY antibodies isolated from eggs of immunized chickens were subjected to affinity purification on Sepharose columns with covalent coupled XPA161. The 24-mer BSA complex was used for immunization of Balb/c mice followed by hybridoma production and monoclonal antibodies (e.g. 528-1D3A9D5A1C). The bound anti-XPA161 antibodies were eluted, neutralized and concentrated as described below. While the following description and examples refer to XPA161, one skilled in the art will appreciate their applicability to SEQ ID NO: 2 as well.

A series of experiments demonstrating the specificity and sensitivity of these new XPA161 antibodies both in immuo precipitation, histochemistry, dot blot and Western blot applications are also exemplified below. As used herein, specificity refers to the ability of the ligand to bind with the peptide. Accordingly, the invention provides the novel peptides of SEQ ID NO: 1 (XPA161) and SEQ ID NO: 2, and defined specific and sensitive TK1 ligands, including poly and monoclonal immunoreagents. The immunoreagents and other ligands can be used alone or together with additional reagents, for example XPA210 immunoreagents, to solve problems of lack of sensitivity and specificity of existing TK1 antibodies and greatly increase the application of TK1 as tumor marker.

More specifically, the determination of serum TK1 as a tumor marker in monitoring hematologic cancers has been used for more than 20 years, as discussed in the Background. However, a major drawback in the commercially available kits is that radio-isotopes are employed and the kits have a limited set of applications. While different monoclonal and polyclonal antibodies directed against TK1 have been used in research, no well established assay for cytosolic or serum TK1 has been commercially developed (10-16). Prior to the invention, the most specific and sensitive TK1 antibodies have been made using the TK1-peptides from the C-terminal region, i.e., 15 or 31-amino acid length fragments (10, 13). Antibodies against the epitope XPA210 have been shown in several studies to be useful for determination of the level of TK1 in cells and serum. It was also found that the enzyme activity and immunological assays of TK1 did not correlate in many cases but appeared to provide complementing information regarding cell proliferation related to cancer diseases.

However, immunologic assay based on a single epitope is less specific and prone to more false positive results as compared with the use of two ligands directed against different epitopes. In the present invention, the described new exposed domain representing the active site domain XPA161 has been defined and shown to give highly specific antibodies that can be used in many different applications. XPA161 and XPA210 antibodies such as the XPA161 IgY and XPA210 IgY and mouse monoclonal IgG provide significant advantages in commercial tumor marker assays. Such antibodies and/or fragments thereof having the TK1 binding function may be used in various methods. For example, a method for determining a level of immunoreactive material in a sample comprises contacting the sample with a ligand having specificity for XPA 161, for example, XPA161 antibody or a fragment thereof, and detecting the amount of bound ligand, i.e., bound antibody or fragment. A method for estimating the likelihood of recurrence of a tumor in an individual comprises determining a level of immunoreactive material in a sample from the individual by contacting the sample with ligand, for example, XPA161 antibody or a fragment thereof, and detecting the amount of bound ligand, and comparing the determined level with a level of immunoreactive material representative of a population of healthy persons or with a level of immunoreactive material previously determined in the same individual. A determined level that is higher than a level associated with a population of healthy persons indicates an increased likelihood of recurrence of a tumor in the individual. Similarly, a determined level that is higher than a level associated with the individual subsequent to previous therapy indicates an increased likelihood of recurrence of a tumor in the individual.

A method for determining cell proliferation in a sample comprises contacting the sample with ligand, for example, the XPA161 antibody or a fragment thereof, and detecting the amount of bound ligand. In a specific embodiment, a level of normal cell or tumor cell proliferation is determined and compared with a previously measured level to monitor anti-proliferation or anti-tumor therapy in the individual. A method of determining a level of inflammation, infection, or tumor cell proliferation in an individual comprises contacting a sample from the individual with ligand, and detecting the amount of bound ligand. Proliferation of tumors cells such as breast tumor, lung tumor, and bladder tumor may be particularly determined and monitored according to the present methods.

In another embodiment, the present invention is directed to methods of performing a health screening test for an individual to detect accelerated cell proliferation. These methods comprise determining a level of immunoreactive material in a sample from the individual by contacting the sample with ligand and detecting the amount of bound ligand, and comparing the determined level with a level of immunoreactive material representative of a population of healthy persons or with a level of immunoreactive material previously determined in the same individual.

Samples for use in such methods may comprise tissue, cells, cell lysates, cell culture media, a body fluid, or the like. Typical body fluids may comprise blood, saliva, urine, mucous, or the like, or any component thereof. In one embodiment, a blood serum or plasma sample is employed.

The amount of bound ligand in a sample may be determined in accordance with various techniques known in the art and may, if appropriate, include separation of the bound ligand from the remainder of the sample in order to quantify the bound ligand.

The invention is also directed to kits comprising the ligand, and more specifically, an antibody or a fragment thereof, having specificity to a peptide as described. Such kits are suitable for use in the various methods described herein, and specifically to determine a level of normal or tumor cell proliferation in an individual using the ligand. The kit may employ any known diagnostic technique, examples of which include, but are not limited to, a histochemistry format and a dot blot format.

The kit may optionally contain at least one additional TK1 ligand, for example a known TKI antibody such as XPA210 antibody. As prior products have shown, there is a need for several specific antibodies interacting with non-competing epitopes on the TK1 antigen. The use of two such specific antibodies often greatly increases the sensitivity and specificity of immunoassays. Thus, an important aspect of the present invention is the design and use of a novel TK peptide described herein (XPA161) for production of a highly specific and complementing TK ligands, in particular antibodies, with specificity for the peptide or a functionally analogous peptide.

EXAMPLES

The following examples are intended to be illustrative of various aspects of the invention and are not intended to be limiting thereof.

Example 1

Preparation of XPA161 and XPA210 Antibodies

Immunization: Two peptides representing amino acids 161 to 183 (AYTKRLGTEKEVEVIGGADKYHS-NH2) (SEQ ID NO: 1), referred to as XPA161 herein, and amino acids 195 to 225 (GQPAGPDNKENCPVPGKPGEAVAARKLFAPQ-OH) (SEQ ID NO: 3), referred to as XPA210 herein, of the human TK1 protein sequence (21) were selected as antigens. In case of XPA161, a cysteine residue was added to the N-terminal Alanine residue. This 24 mer peptide was coupled to KLH or BSA using the free sulfyryl group and a bifunctional crosslinker 3-maleimidobenzoic acid N-hydroxysuccinimide ester (MBS). XPA210 was coupled to KLH using glutaraldehyde. The peptides (>96% pure) were synthesized and the cross linking performed by NeoMPS Inc., San Diego, Calif. as described (see www.neompls.com). Approximately 100 μg peptide complex was re-suspended in 500 μl PBS (pH 7.2) and mixed with an equal volume of complete Freund's adjuvant (Sigma, St. Louis, USA). The mixture was injected into the pectoral muscle of American-laying hens or subcutaneous on Blab/c mice in case of XPA161. Three booster injections with 50-100 μg antigen mixed with incomplete Freund's adjuvant were given at 2, 4 and 6 weeks. Eggs were collected daily and kept at 4° C. until immunoglobulins were extracted or blood was collected from the mice and tested by ELISA as described below.

Preparation of crude and affinity purified XPA161 IgY and XPA210 IgY: One part egg yolk was diluted with 3 parts 0.1 M NaHPO$_4$, pH 7.5 and 1 part 17.5% polyethylene glycol (PEG) giving a final concentration of 3.5% PEG. After slow stirring lipids were precipitated by centrifugation, the supernatant was filtered through a coarse paper filter paper and in this form the crude IgY could be stored at 4° C. The crude IgY fraction was desalted by passage over a P10 gel filtration column equilibrated with 0.025 M Tris-HCL, 0.137 M NaCl, pH 7.6 (TBS), and purified by affinity chromatography. The XPA161 and XPA210 affinity media were produced essentially as described (12) briefly as follows: to each ml of HCl treated CNBr-activated Sepharose 4 fast flow (GE Health Care, Uppsala), 1-2 mg XPA161 or XPA210 was added in the coupling buffer, 0.2 M NaHCO$_3$, 0.5 M NaCl, pH 8.3, and mixed end over end over night. The reactions were blocked by treatment with 0.2 M Tris-HCl, pH 8.0 at room temperature for 2 hrs. This media was then washed with 0.1 M acetate, 0.5 M NaCl, pH 4 alternating with washes with the coupling buffer. Desalted PEG treated IgY fractions were applied to the affinity media (approx. 100 mg per ml), washing was carried out with 0.1 M Tris-HCl, pH 8.0, 0.5 NaCl, until the absorbance at 280 nm was below 0.02. Purified anti-XPA161 or XPA210 IgY was eluted from the columns with the ActiSep solution (see sterogene.com, product ID 9701-01) and then passed over a Sephadex G25 column equilibrated with PBS. The purified antibody solutions were stored frozen at −20° C.

Preparation of anti XPA161 monoclonal antibodies: Female Balb/c mice were immunized with the XPA161-BSA complex as described above. At and after 3 booster immunizations, splenocytes were isolated and fused with mouse myeloma cell line SP 2/0. The resulting hybridomas were selected by screening the supernatants in ELISA plates as described below. Positive wells were identified and subjected to 3-4 rounds of sub-cloning. Positive monoclonal cells were expanded and a large batch of supernatants prepared, lyophilized and used for the test described. Enzyme linked immunosorbent assay (ELISA): Crude XPA161 IgY, supernatants from mouse hybridomas or XPA210 IgY were tested using an ELISA alkaline phosphate detection system (Vector Laboratories, CA, USA) with 96-well plates coated with XPA161 or XPA210 (0.05 μg/well). The antigens were dissolved in NaHCO$_3$ buffer, pH 9.6. Wells were blocked with 1% BSA in TBS for 2 hr, washed with TBS with 0.1% Tween 20. Crude IgY fractions were added to peptide coated or uncoated wells, incubated for 2 hr at 37° C. and then washed with the same buffer. The wells were then incubated with biotinylated anti-chicken IgG (Jackson ImmunoResearch Lab, USA, code nr 703-066-155) or anti mouse IgG, washed and reacted with Avidine-HRP conjugated anti IgG antibodies, and washed. TMB substrate (SIGMA, T8665) was then added. The absorbance at 495 nm was determined in an ELISA plate reader as described. The identification of the fractions with the highest crude as well as purified XPA161 and XPA210 was done with this ELISA method. This procedure was used to identify the wells with hybridoma cells producing anti-XPA161 mouse IgG.

Example 2

Immunoprecipitation Reactions with XPA210 IgY and XPA161 IgY

Preparation of cell extracts: Human lymphoblastoid cells Cem wild-type (CEM TK1$^+$), and CEM TK1$^-$ cells, selected for bromodeoxyuridine resistance were cultured as described (24). Cells were harvested by centrifugation and the cell pellets (40×10$^6$/ml) were lysed using a buffer containing 10 mM Tris-HCl, pH 7.6, 13.7 mM NaCl and 1 mM phenylmethylsulfonyl fluoride (PMSF), 0.25% NP-40 for 30 min at 4° C., followed by centrifuging at 16,000×g for 10 mM at 4° C. The supernatant was stored at −80° C. before use.

Immunoprecipitation: To test if the antibodies inhibited the activity of human TK1, immunoprecipitation was performed as previously described (12), with slight modifications. To extracts from CEM TK1$^+$ and CEM TK1$^-$ cells (containing 250 μg of protein), 2 μg of the purified XPA161 IgY antibody or 1 μg of XPA210 IgY were added to 50 μl TBS buffer, containing 1 mg/ml BSA, 1 mM PMSF. These solutions were incubated for 1 h at 4° C., then 30 μl of HiTrap IgY purification HP medium from GE Health Care Uppsala, was added and mixed gently. The solutions were subjected to a 30 second centrifugation and supernatants collected (s). The beads were washed four times with TBS buffer as described above and re-suspended with an equal volume of TBS buffer. TK1 activities were determined both in the supernatants and bead (p) fractions using a buffer containing 0.1 M Tris-HCl (pH 7.6), 137 mM NaCl, 5 mM ATP, 2.5 mM $MgCl_2$, 5 mM NaF, 2 mM beta-mercaptoethanol, 1 μl of [$^3$H]-thymidine (specific activity 0.74 TBq) and 30 μM unlabelled thymidine for 30 min at 37° C. Product formation was determined as described (10, 12) and TK1 activity was expressed in counts CPM per min per total protein.

Figure 2:
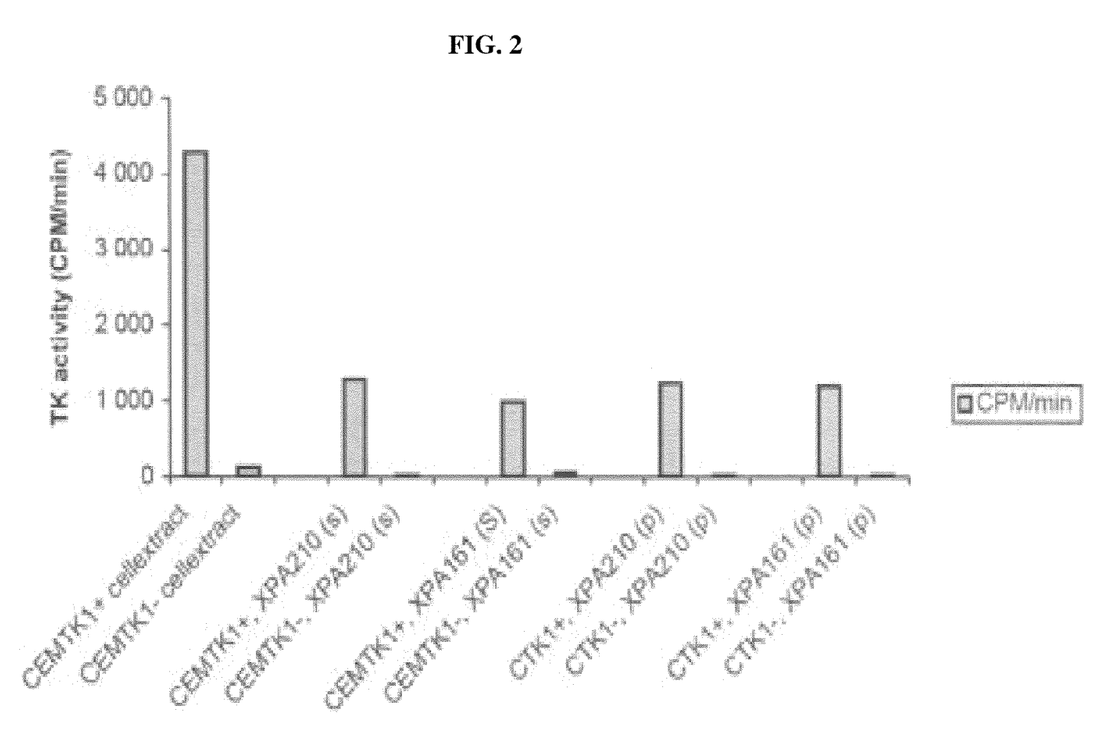

The results (FIG. 2) showed that XPA210 IgY as well as XPA161 IgY bound a substantial part of the TK1 in the extracts, since the activities in the supernatant fractions decreased by more than 70%. TK1 activities were found in the pelleted and washed bead fractions, in both cases and apparently binding of XPA 161 IgY or XPA 210 IgY did not block enzyme activity.

Example 3

PAGE, SDS/PAGE and Enhanced Chemiluminescence (ECL) Western Blotting

Native-PAGE (NOVEX, Invitrogen Living Science, Sweden) was used to separate the native tetrameric form of TK1, followed by ECL immuno blotting using the purified anti-TK1, XPA161 and XPA210 IgY antibodies. Twenty μg protein from CEM TK1$^+$ and CEM TK1$^-$ cell extracts were added to an equal volume of a non denaturing sample buffer (125 mM Tris-HCl, pH 8.8, 137 mM NaCl, 20% glycerol) and then directly applied to a 4-10% gradient native-PAGE gel. SDS-PAGE gels were used to separate and detect the monomeric 25 kDa form of the TK1 polypeptide in these cell extracts using recombinant human TK1 as positive controls (2, 1, 0.5 ng TK1, respectively). Forty μg of CEM TK1+ and TK1− proteins were analyzed on 12% gels after denaturation in SDS sample buffers (12). Electrophoresis was performed according to the manufacturer's protocol (Bio-Rad Inc). After electrophoretic transfer of proteins to the PVDF membrane, they were blocked in a TBS buffer containing 10% non-fat milk. TK1 was then probed with purified XPA210, XPA161 IgY and crude mouse monoclonal anti XPA 161 antibodies (0.2 μg/ml and 2 μg/ml, respectively) and incubated overnight at 4° C. Subsequently, the membranes were incubated with anti-chicken IgY or anti mouse IgG biotinylated antibody conjugates, followed by an avidin-HRP conjugate and ECL detection (12).

Figure 3A:
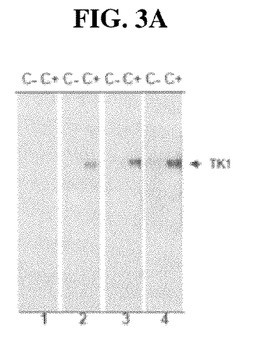
Figure 3B:
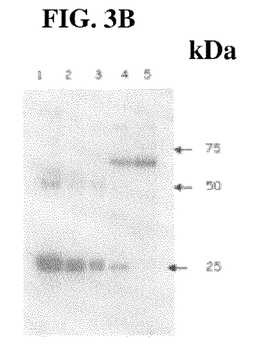

FIG. 3A shows that there was only one immunoreactive band with migration properties similar to the TK1 tetramer (12) detected in extracts from CEM TK1$^+$ cells using both XPA161 IgY and XPA210 IgY as primary antibodies. There were no bands in CEM TK1$^-$ cell extracts or when the primary antibodies were not added. Thus, these results demonstrate that XPA161 IgY and XPA210 IgY are specific immunoreagents for the native tetramer TK1. FIG. 3B shows that the anti-XPA 161 crude mouse IgG fraction reacted with recombinant TK1 well below 0.5 ng/10 μl cell extract and detected a 25 kDa TK1 polypeptide in CEMTK+ but not TK-cell extracts. There were one additional strong band at about 60 kDa but this polypeptide was also seen with out addition of primary antibodies and thus represents an artifact. In addition there were also some minor bands stained in the extracts corresponding to 35 and 85 kDa, respectively. These results show that the mouse hybridoma supernatant (528-1D3A9D5A1C) reacts specifically with denatured recombinant TK1 as well as TK1 in cell extracts and can detect TK1 levels below 1/10 000 total cellular protein.

Example 4

Immuno Histochemistry and Immuno Cytochemistry with XPA-161 IgY and XPA210 IgY

Figure 4:
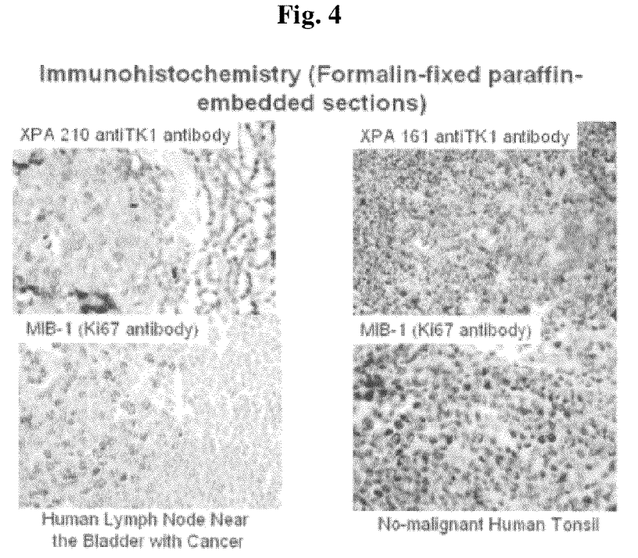
FIG. 4 shows immunohistochemistry staining of lymph nodes and human tonsils with XPA161 IgY, XPA210 IgY and MIB-1. The procedures for the staining reactions are described in Example 4.

Formalin-fixed and paraffin embedded human tonsil and lymph node near a bladder with cancer were stained with anti TK1 or Ki67 (MIB-1) antibodies (1:100 as recommended by Dako Immunocytometry Inc.) as described previously (13) using Avidin-biotinylated peroxidase complex and the DAB chromogen. The results (FIG. 4) showed that proliferating cells in the tonsil and the lymph node were stained in the cytoplasm with both XPA161 and XPA210 anti TK1 antibodies. Similar results were obtained using the anti XPA 161 mouse IgG supernatants for staining human tonsil sections. The Ki67/MIB-1 antibodies reacted with the same set of cells but in this case staining was in the nucleus.

Figure 5:
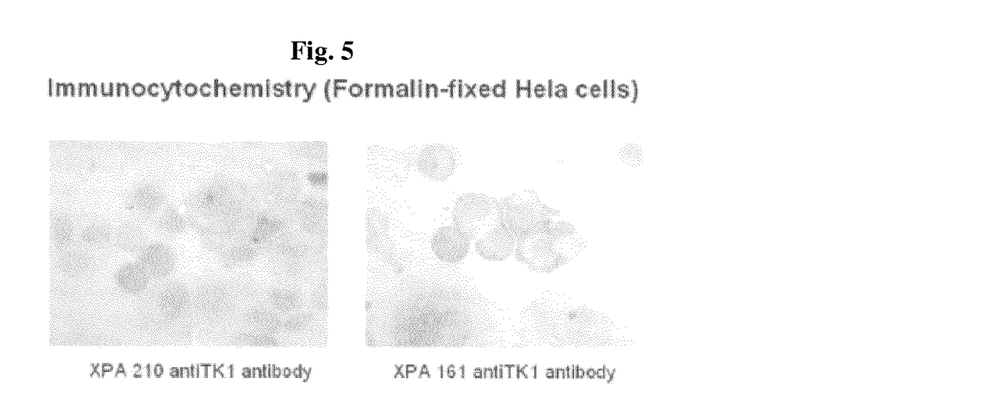
FIG. 5 shows immunocytochemistry staining of cultured Hela cells with XPA161 IgY and XPA210 IgY. The procedures for the staining reactions are described in Example 4.

Formalin-fixed cultured Hela cells were also stained with the XPA161 and XPA210 anti TK1 antibodies using the Avidin-biotinylated peroxidase complex and the DAB chromogen (13, 14). FIG. 5 shows the cytoplasmic staining of Hela cells with both these anti TK1 antibodies. These results demonstrate that XPA161 IgY and XPA210 IgY react specifically with proliferating cells both in tissue sections and with cultured cells.

Example 5

Determination of Serum TK1 (S-TK1) Levels Using Dot Blotting and ECL

Serum samples from patients with histological diagnosed breast cancer (16, 22) and lung cancer (26) obtained from Hubei Cancer Hospital, China and breast cancer samples (11, 17) from the Karolinska Hospital, Sweden were analyzed by dot blotting, essentially as described earlier (10, 12). Serum sample (3 μl) from the cancer patients were dotted onto ECL cellulose membranes. Recombinant human TK1 (1, 12) was dotted in varying concentrations and used as positive controls. Sera from healthy persons were used as negative controls (data not shown) and there was no apparent reactivity without primary antibody (data not shown).

Figure 6:
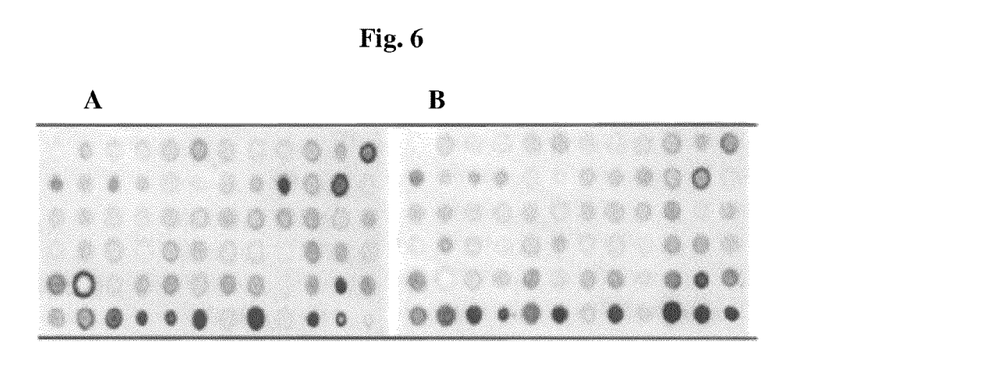
FIG. 6 shows dot blot analysis of sera from cancer patients. Serum samples (3 µl) from cancer patients were applied on ECL cellulose membranes. Row 1, slots 1-12, row 2, slots 1-12, and row 3, slots 1-3 are sera of breast cancer patients from Hubei Cancer Hospital, China. Row 3, slots 4-12, row 4, slots 1-12, and row 5, slots 1-9 are sera of lung cancer patients from Hubei Cancer Hospital, China. Row 5, slots 10-12 and row 6, slots 1-9 are sera of breast cancer patients from the Karolinska Hospital, Stockholm, Sweden. Row 6, slots 10-12 are human recombinant TK1 samples (approx. 6-0.3 pg) used as positive and calibration controls. "A" shows detection with XPA210 IgY (approx. 0.2 µg/ml), and "B" shows detection with XPA161 IgY (approx. 0.3 µg/ml).

FIG. 6 shows that XPA210 IgY reacted with a subset of the sera from cancer cells as well as with recombinant TK1. These results could be used to determine the levels of TK1 immuno-reactive material as described earlier (11, 17). The dot blot results with XPA161 showed a somewhat different but also overlapping pattern. Most sera are positive or negative with both antibodies but there are several which differ, e.g., row 2, well 9; row 5, well 2. Furthermore, XPA161 IgY appears to react more efficiently with recombinant TK1.

The results demonstrate that XPA161 and XPA210 IgY are reacting with recombinant TK1 as well as serum TK in sera from several different type of patients. Both antibodies react with the same sera in most cases but in a minor fraction it was clearly differing. Similar dot blot results with recombinant TK1 and some normal and tumor sera were obtained using the anti-XPA161 mouse IgG supernatants (e.g. 528-1D3A9D5A1C). Thus, by the use of both XPA161 IgY and mouse IgG and XPA210 IgY, complementing information can be obtained which most likely will improve the diagnostic capacity of TK determinations in monitoring and predicting recurrence of cancer diseases.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments described in the specification and/or the examples. As one of ordinary skill in the art will readily appreciate from the disclosure of the present invention, additional embodiments, presently existing or later to be developed, that perform substantially the same function or achieve substantially the same result as the corresponding embodiments described herein may be utilized according to the present invention. Accordingly, the appended claims are intended to include within their scope such additional embodiments.

REFERENCES

1. Eriksson et al, "Structure and function of cellular deoxynucleoside kinases, CMLS," *Cell Mol. Life. Sci.*, 59: 1327-1346, 2002.
2. Gronowitch et al, "The use of serum deoxythymidine kinase as a prognostic marker, and in the monitoring of patients with non-Hodgkin's lymphoma," *Br. J. Cancer*, 47: 487-495, 1983.
3. Hallek et al, "Thymidine kinase: a tumor marker with prognostic value for non-Hodgkin's lymphoma and a broad range of potential clinical applications," *Ann. Hematol*, 65: 1-5, 1992.
4. Hallek et al, "Elevated serum thymidine kinase levels identify a subgroup at high risk of disease progression in early, nonsmoldering chronic lymphocytic leukemia," *Blood*, 93: 1732-1737, 1999.
5. Broet et al, "Thymidine kinase as a proliferative marker: Clinical relevance in 1,692 primary breast cancer patients," *J Clin Oncol*, 19:2778-2787, 2000.
6. Foekens et al, "Thymidine kinase and thymidylate synthase in advanced breast cancer: response to tamoxifen and chemotherapy," *Cancer Res*, 61:1421-1425, 2001
7. Öhrvik et al, "Sensitive nonradiometric method for determining thymidine kinase 1 activity," *Clin Chem*, 50:1597-1606, 2004.
8. Öhrvik et al, "Method for determination of thymidine kinase 1 activity and the use thereof," U.S. Patent Publication No. US2006/0035295.
9. see biovica.com.
10. He et al, "Characterization of a peptide antibody against a C-terminal part of human and mouse cytosolic thymidine kinase, which is a marker for cell proliferation," *Europ. J. Cell Biol.*, 70: 117-124, 1996.
11. He et al, "The clinical significance of thymidine kinase 1 measurement in serum of breast cancer patients using anti-TK1 antibody," *Int. J. Biol. Marker*, 15: 139-146, 2000.
12. Wu et al, "Production and characterization of a novel chicken IgY antibody raised against C-terminal peptide from human thymidine kinase 1," *J. Immuno. Method*, 277: 157-169, 2003.
13. Mao et al, "A comparative study. Immunohistochemical detection of cytosolic thymidine kinase and proliferating cell nuclear antigen in breast cancer," *Cancer Invest*, 20: 922-931, 2002.
14. Wang et al, "Investigation on cell proliferation with new antibody against thymidine kinase 1," *Analysis Cell. Pathology*, 23: 11-19, 2001.
15. Zou et al, "The half-life of cytosolic thymidine kinase in serum measured by ECL dot blot: a potential marker for monitoring the response to surgery of patients with gastric cancer," *J. Biolog. Marker*, 17:135-140, 2002.
16. Kuroiwa et al, "Specific recognition of cytosolic thymidine kinase in the human lung tumor by monoclonal antibody raised against recombinant human thymidine kinase," *J. Immuno. Methods*, 253:1-11, 2001.
17. He et al, "Thymidine kinase 1 in serum predicts increased risk of distant or loco-regional recurrence following surgery in patients with early breast cancer," *Anticancer Res*, 26:4753-4759, 2006
18. see biosstk.com.
19. Welin et al, "Structures of thymidine kinase 1 of human and mycoplasma origin," *Proc. Natl. Acad. Sci. USA*, 102: 17970-17975, 2004.
20. Ke et al, "Mitotic degradation of human thymidine kinase 1 is dependent on the anaphase-promoting complex/cyclosome-CDH1-mediated pathway," *Mol Cell Biol.*, 24(2): 514-26, 2004.
21. Flemington et al, "Sequence, structure and promoter characterization of the human thymidine kinase gene," *Gene*, 52:267-277, 1987.
22. Wu et al, "A new cell proliferating marker: Cytosolic thymidine kinase as compared to proliferating cell nuclear antigen in patients with colorectal carcinoma," *Anticancer Res.*, 20:4815-4820, 2000.
23. Karlstrom et al, "Molecular forms in human serum of enzymes synthesizing DNA precursors and DNA," *Mol Cell Biochem.*, 18:23-35, 1990.
24. Tornevik et al, "Cytotoxicity of 3'-azido-3'-deoxythymidine correlates with 3'-azidothymidine-5'-monophosphate (AZTMP) levels, whereas anti-human immunodeficiency virus (HIV) activity correlates with 3'-azidothymidine-5'-triphosphate (AZTTP) levels in cultured CEM T-lymphoblastoid cells," *Biochem Pharmacol*, 49:829-837, 1995.

What is claimed is:

1. An isolated ligand having specificity for a peptide consisting of an amino acid sequence selected from the group consisting of SEQ ID NO:1 and SEQ ID NO:2.

2. The ligand of claim 1, wherein the ligand is an antibody.

3. The ligand of claim 2, wherein the ligand is a monoclonal antibody.

4. The ligand of claim 2, wherein the antibody is covalently coupled to a carrier.

5. The ligand of claim 1, wherein the ligand is a fragment of an antibody.

6. A method of determining a level of immunoreactive material in a sample, comprising contacting the sample with the ligand of claim 1 and detecting the amount of bound ligand.

7. The method of claim 6, wherein the ligand is an antibody or fragment thereof.

8. The method of claim 6, wherein the sample comprises tissue, cells, cell lysates, cell culture media, or a body fluid.

9. The method of claim 8, wherein the sample comprises blood serum or plasma.

10. A method of estimating the likelihood of recurrence of a tumor in an individual, comprising determining a level of immunoreactive material in a sample from the individual by contacting the sample with the ligand of claim 1 and detecting the amount of bound ligand, and comparing the determined level with a level of immunoreactive material representative of a population of healthy persons or with a level of immunoreactive material previously determined in the same individual.

11. The method of claim 10, wherein the ligand is an antibody or fragment thereof.

12. The method of claim 10, wherein the sample comprises tissue, cells, cell lysates, cell culture media, or a body fluid.

13. The method of claim 12, wherein the sample comprises blood serum or plasma.

14. A method for determining cell proliferation in a sample, comprising contacting the sample with the ligand of claim 1 and detecting the amount of bound ligand.

15. The method of claim 14, wherein the ligand is an antibody or fragment thereof.

16. The method of claim 14, wherein the sample comprises tissue, cells, cell lysates, cell culture media, or a body fluid.

17. A method of determining a level of inflammation, infection, or tumor cell proliferation in an individual, comprising contacting a sample from the individual with the ligand of claim 1 and detecting the amount of bound ligand.

18. The method of claim 17, wherein the ligand is an antibody or fragment thereof.

19. The method of claim 17, wherein the sample comprises tissue, cells, cell lysates, cell culture media, or a body fluid.

20. The method of claim 17, wherein a level of normal cell or tumor cell proliferation is determined and compared with a previously measured level to monitor anti-proliferation or anti-tumor therapy in the individual.

21. A method of performing a health screening test for an individual to detect accelerated cell proliferation, comprising determining a level of immunoreactive material in a sample from the individual by contacting the sample with the ligand of claim 1 and detecting the amount of bound ligand, and comparing the determined level with a level of immunoreactive material representative of a population of healthy persons or with a level of immunoreactive material previously determined in the same individual.

22. The method of claim 21, wherein the ligand is an antibody or fragment thereof.

23. The method of claim 21, wherein the sample comprises tissue, cells, cell lysates, cell culture media, or a body fluid.

24. The method of claim 23, wherein the sample comprises blood serum or plasma.

25. Kit comprising the ligand of claim 1 as one ligand, to determine a level of normal or tumor cell proliferation in an individual using the ligand.

26. The kit of claim 25, wherein the ligand is an antibody or fragment thereof.

27. The kit of claim 25, comprising at least one additional ligand having a TK1 specificity different from the TK1 specificity of the one ligand.

28. The kit of claim 25, comprising a histochemistry format.

29. The kit of claim 25, comprising a dot blot format.

* * * * *